United States Patent [19]
Beck et al.

[11] Patent Number: 5,814,345
[45] Date of Patent: Sep. 29, 1998

[54] IMMUNE SUPPRESSIVE PRODUCT

[75] Inventors: Lee R. Beck, Lebanon; Ralph J. Stolle, Oregonia, both of Ohio

[73] Assignee: Stolle Research & Development Corporation, Cincinnati, Ohio

[21] Appl. No.: 460,277

[22] Filed: Jun. 21, 1995

Related U.S. Application Data

[60] Division of Ser. No. 815,630, Dec. 30, 1991, which is a continuation-in-part of Ser. No. 431,639, Nov. 6, 1989, Pat. No. 5,130,128, and Ser. No. 177,223, Apr. 4, 1988, Pat. No. 4,956,349, said Ser. No. 431,639, is a continuation-in-part of Ser. No. 161,039, Feb. 26, 1988, Pat. No. 4,879,110, said Ser. No. 161,039, and Ser. No. 177,223, each is a continuation-in-part of Ser. No.1,848, Jan. 9, 1987, Pat. No. 4,897,265, which is a division of Ser. No. 546,162, Oct. 27, 1983, Pat. No. 4,636,384, which is a continuation-in-part of Ser. No. 384,625, Jun. 3, 1982, abandoned.

[51] Int. Cl.$^6$ ..................................................... A61K 35/20
[52] U.S. Cl. ................... 424/535; 424/184.1; 424/193.1; 424/278.1; 424/520; 530/832; 530/868
[58] Field of Search .............................. 424/184.1, 193.1, 424/278.1, 520, 535; 530/832, 868

[56] References Cited

U.S. PATENT DOCUMENTS

| Re. 33,403 | 10/1990 | Stolle et al. | 424/87 |
|---|---|---|---|
| 4,284,623 | 8/1981 | Beck | 424/85 |
| 4,469,677 | 9/1984 | Michael et al. | 424/91 |
| 4,636,384 | 1/1987 | Stolle et al. | 424/87 |
| 4,732,757 | 3/1988 | Stolle et al. | 424/87 |
| 4,879,110 | 11/1989 | Beck et al. | 424/85.8 |
| 4,956,349 | 9/1990 | Beck | 514/54 |
| 5,130,128 | 7/1992 | Stolle | 424/85.8 |

FOREIGN PATENT DOCUMENTS

| 0 107 832 | 5/1984 | European Pat. Off. | A61K 39/35 |

OTHER PUBLICATIONS

Hanson, D.G. et al. *Inhibition of Specific Immune Responses By Feeding Protein Antigens*, Int. Archs. Allergy Appl. Immun. 55:526–532 (1977).

Higgins, P.J. et al., *Suppression of Experimental Autoimmune Encephalomyelitis By Oral Administration Of Myelin Basic Protein And Its Fragments*, J. Immunol. 140:440–445 (1988).

Lafont, S. et al., *Abrogation By Subsequent Feeding Of Antibody Response, Including IgE In Parenterally Immunized Mice*, J. Exp. Med. 155:1573–1578 (1978).

Liu, Fu–Tong et al., *Immunological Tolerance To Allergenic Protein Determinants: A Therapeutic Approach For Selective Inhibition of IgE Antibody Production*, Proc. Nat'l Acad. Sci., U.S.A., 76:1430–1434 (1979).

Mowat, A. McI., *The Role of Antigen Recognition And Suppressor Cells In Mice With Oral Tolerance To Ovalbumin*, Immunology 56:253–260 (1985).

Nagler–Anderson, C. et al., *Suppression of Type II Collagen––Induced Arthritis By Intragastric Adminstration Of Soluble Type II Collagen*, Proc. Nat'l Acad. Sci. 83:7443–7446 (1986).

Patterson, R., *Allergen Immunotherapy With Modified Allergens*, J. Allergy Clin. Immunol. 68:85–90 (1981).

Supplementary Partial European Search Report for Application No. EP 91/909 691 (Jun. 1, 1993).

*Primary Examiner*—Laurie Scheiner
*Attorney, Agent, or Firm*—Sterne, Kessler, Goldstein & Fox P.L.L.C.

[57] ABSTRACT

An immune suppressive product prepared by injecting an allergen or a mixture of allergens into the body of milk-producing species. Said product being the milk or a polypeptide subfraction of milk obtained from the allergen treated host. The immune suppressive product(s) is milk and or the polypeptide fractions contained therein, which is ostensively free of the intact allergen or allergens used for the treatment of the host. The immune suppressive factor(s) being a subfraction of the allergen used for the treatment. A method of preparing immune suppressive polypeptides from intact allergens, which involves injection of the specific intact allergens into a milk-producing species, collecting the immune suppressive polypeptide fractions of the intact allergens from the milk of the treated host. The immune suppressive milk containing said polypeptide fractions, and/or the polypeptide fractions obtained from said milk, are nonreactive in animals and humans as allergens. Said factor(s), however, are highly effective in preventing or alleviating allergic reactions.

1 Claim, No Drawings

IMMUNE SUPPRESSIVE PRODUCT

CROSS-REFERENCE TO RELATED APPLICATIONS

This application is a division of application Ser. No. 07/815,630, filed Dec. 30, 1991, (status: pending) which is a continuation-in-part of U.S. patent application Ser. No. 07/431,639, filed Nov. 6, 1989, now U.S. Pat. No. 5,130,128 and a continuation-in-part of U.S. patent application Ser. No. 07/177,223, filed Apr. 4, 1988 now U.S. Pat. No. 4,956,349; U.S. application Ser. No. 07/431,639 is a continuation-in-part application of U.S. application Ser. No. 07/161,039, filed Feb. 26, 1988, now U.S. Pat. No. 4,879,110; both U.S. application Ser. No. 07/161,039 and U.S. application Ser. No. 07/177,223 are continuation-in-part applications of U.S. patent application Ser. No. 07/001,848, filed Jan. 9, 1987, now U.S. Pat. No. 4,897,265, which is a divisional of U.S. patent application Ser. No. 06/546,162, filed Oct. 27, 1983, now U.S. Pat. No. 4,636,384, which is a continuation-in-part of U.S. patent application Ser. No. 06/384,625, filed Jun. 3, 1982, now abandoned.

The contents of all of the above applications are all fully incorporated herein by reference.

FIELD OF THE INVENTION

This invention is directed to the discovery of polypeptide fractions in milk which contain peptides derived from allergens administered to a milk-producing animal. These fractions are useful in suppressing allergic responses in humans and animals.

BACKGROUND OF THE INVENTION

The allergic reaction in man and animals has been extensively studied and the basic immune mechanisms involved are well known. The generic name for molecules that cause an allergic reaction is allergen. There are numerous species of allergens. Common examples include plant pollens, bee venom, house dust, animal dander, and a wide array of food proteins. Many allergens are protein or polypeptide in nature, as proteins and polypeptides are generally more antigenic than carbohydrates or fats. The allergic reaction occurs when tissue-sensitizing immunoglobulin of the IgE type reacts with foreign allergen. The IgE antibody is bound to mast cells and/or basophils, and these specialized cells release chemical mediators of the allergic reaction when stimulated to do so by divalent antigens bridging the antibody molecules. Histamine, platelet activating factor, arachidonic acid metabolites, and serotonin are among the best known mediators of allergic reactions in man.

The symptoms of the allergic reaction vary, depending on the location within the body where the IgE reacts with the antigen. If the reaction occurs along the respiratory epithelium the symptoms are sneezing, coughing and asthmatic reactions. If the interaction occurs in the digestive tract, as in the case of food allergies, abdominal pain and diarrhea are common. Systematic reactions, for example following a bee sting, can be severe and often life threatening.

The preferred, but frequently impossible, method of relieving allergies is allergen avoidance. Failing that, there are two medical approaches to allergy control, both with an approximate 60 to 85% efficacy rate (Aas K., Allergy 37:1–14 (1982)). The most common approach to the medical treatment of allergies is to treat the symptom. Drugs known to block the effects of the chemical mediators of the allergic reactions, including antihistamines, are used to control the severity of the allergic symptoms. These drugs, however, do nothing to prevent the allergic reaction and the liberation of the chemical mediators, and do nothing to prevent or diminish allergic responses to subsequent allergen exposure.

Another approach is to prevent the allergic reaction by desensitizing the allergic host. This is accomplished by giving repeated small doses of the reactive allergen. The treatment usually involves injecting the allergens under the skin. Treatment with reactive allergens, more appropriately called immunotherapy, is believed to increase the concentration of antibodies of the IgG type against the allergen. The IgG antibody competes with the IgE antibody for allergen binding, and this competitive antibody somehow neutralizes, arrests, or blocks the action of the tissue sensitizing IgE antibody, although a distinct correlation between blocking antibody and amelioration of symptoms has not been definitely proven (Mailing, H. J., (ed.), Immunotherapy Position Paper, Allergy (Supp.) 6, 43:9–33 (1988)). This rationale, although generally accepted, is not fully understood, and does not reflect the complex interactions and events that accompany the IgG response. For example, other effects of immunotherapy that may be involved with relief of symptoms include suppression of IgE, increase in blocking IgA and IgG in secretions, reduced basophil reactivity/sensitivity, and reduced lymphocyte responsiveness to allergens. All of these changes may not occur in every patient, and those related to actual symptom relief have not been conclusively defined (Norman, P. S., J. Allergy Clin. Immuno. 75:531–545 (1985)).

Immunotherapy using reactive allergen is dangerous because the sensitized host is actually treated with the molecules capable of eliciting an allergic response. The treatment is started with extremely low does to avoid inducing a severe reaction. The antigen concentration required for 50% histamine release from peripheral basophils of an allergic individual varies 10,000 fold from patient to patient (Norman, P. S., J. Allergy Clin. Immunol. 75:531–545 (1985)). If no adverse reaction occurs, higher doses are given. The injection may cause severe allergic reactions and extreme care must be taken. Only experienced doctors can administer this treatment because if a severe reaction occurs immediate medical treatment must be given to control the symptoms of the allergic reaction. Desensitization is an expensive, painful, and time consuming process (Aas K., Allergy 37:1–14 (1982)), therefore, only the most severe allergies are treated by this method (Malling, H. J., ed., Immunotherapy Position Paper, Allergy (Supp.) 6, 43:9–33 (1988)).

Modifying allergens to eliminate their allergenicity, or ability to induce an IgE-mediated response, while preserving their immunogenicity, or their ability to elicit the protective IgG response, has been under investigation for years. Polymerized antigens have been evaluated with the theory that they would display reduced antigenicity due to concealed antigenic determinants, a lower molecular concentration hence decreased bridging opportunity on a weight basis, and slower diffusion through the tissues (Patterson R., J. Allergy Clin. Immunol. 68:85–90 (1981)). Allergen conjugates have been studied with a variety of allergens in attempts to selectively inhibit the formation of IgE antibodies while normal IgM and IgG responses to the antigen occurred (Lee, W. Y. et al., Imm. Rev. 41:200–217 (1978)). Conjugates with a glutamic acid/lysine copolymer may be acting specifically on IgE lymphocytes, on suppressor and/or helper T cells, or a combination of mechanisms may be in effect (Liu, F. T. et al., Proc. Natl. Acad. Sci. USA 76:1430–1434 (1979)).

Modifications that decrease the size of the allergen in efforts to eliminate their allergenicity have also been attempted. It has been proposed that limited proteolysis may actually reveal suppressor determinants on allergen molecules (Mowatt A. M., *Immunology* 56:253–260 (1985)).

Polypeptide fractions of allergens and the use of enzymes to break down the parent proteins is not new (King, T. P., *Advances in Immunology* 23:77 (1976)). U.S. Pat. No. 4,469,677 teaches the use of polypeptide fractions prepared from allergens for desensitization of allergic humans and animals. The polypeptide fractions are prepared by digesting allergens with proteolytic enzymes. Following the enzymatic digestion procedure, the enzymes and residual parent allergens must be removed from the polypeptide subfractions. The specific structure of the polypeptide fractions is dependent on the enzymes used for the digestive process. However, this is a synthetic process that requires preselection of the enzymes used for the digestive process. The polypeptide fraction is produced by controlled proteolytic digestion of the polypeptide allergen. Although this represents an improvement over using the reactive antigens, the treatment still requires frequent and painful injections.

The function of the polypeptide fractions for suppressing immune function are structure dependent. see Unanue, E. R. et al., *Science* 236:551–557 (1977) for a review of the structure dependence of polypeptide fractions of proteins in the immune response.

The structure of the polypeptide fractions of Michael is limited because the selection of enzymes is based on a limited understanding of which enzymes are most important.

The development of oral "tolerance" is a normal phenomenon, and a necessary function in response to the variety of foreign antigens consumed in the diet. Oral tolerance is initiated by a special class of T lymphocytes and their products, and it results in systematic suppression of the IgE-mediated hypersensitivity reaction. Variable responses of other components of the immune system have been reported to occur during induction of the tolerized state, so that the actual mechanism has not been succinctly defined.

In addition, animal studies have shown an actual enhancement of IgE production in response to intragastric administration of pollen extracts (Henderson, D. C. et al., *Int. Archs. Allergy Appl. Immun.* 79:66–71 (1986)). Although this may be a dose-related phenomenon, conflicting results were reported from two studies where 20 mg ovalbumin was administered orally to parenterally immunized mice, with IgE increased in one study (Handson, D. G. et al., *Int. Arch. Allergy Appl. Immun.* 55:256–532 (1977)) and decreased in the other (Lafont, S. et al., *J. Exp. Med.* 155:1573–1578 (1982)).

Some investigators have concluded that recognition of antigenic determinants varies between parenterally and orally induced suppressor T cells. Suppressor cells resulting from feeding antigen were able to recognize different forms of the antigen, while parenterally induced suppressor T cells were specific for the molecular confirmation to which they initially responded (Mowatt, A. M., *Immunology* 56:253–260 (1985)). If this phenomenon is exhibited by a majority of antigens, it would further warrant the use of oral immunotherapy.

The problem with administering allergens orally to allergic subjects is that severe immune reactions may occur following treatment by this route as well. Anaphylaxis, relapse, urticaria, rectal bleeding, and anaphylactic shock have all been reported following oral immunotherapy (Platts-Mills, T. A. E., *J. Allergy Clin. Immunol.* 80:129–132 (1987)). In addition, oral treatment requires significantly larger doses than parenteral therapy, due to the action of the digestive tract enzymes upon the allergens. Individual responses to the ingested antigens may vary, however, so that more or less intact allergen may be represented to the gastrointestinal mucosa from the same dose given to different subjects, increasing the risk of inappropriate dosing.

Nonallergenic fractions of allergens can be given orally without concern for severe immune reactions; however, for reasons that are not clearly understood, oral administration of the polypeptide fractions of some allergens, including those prepared in the Michaels patent (U.S. Pat. No. 4,469,677) are not effective in causing desensitization. Studies of the immune response to feeding other modified proteins are limited, with varying results. Collagen-induced arthritis in mice was suppressed by feeding native type II collagen but not if the denatured molecule was fed (Nagler-Anderson, C. L. et al., *Proc. Natl. Acad. Sci. USA* 83:7443 (1986)). In a study of another autoimmune disease, both the disease-producing and nondisease-producing fragments and decapeptides of the myelin base protein were capable of eliciting immune suppression following oral treatment in rats (Higgins, P. J. et al., *J. Immunology* 140:440–445, (1988)). Results from a mouse study evaluating induction of oral tolerance with both natural and denatured ovalbumin identical suppression of delayed type hypersensitivity response to each form (Mowat, A. M., *Immunology* 56:253–260 (1985)).

One factor that may be involved in the failure of some molecular fragments to effectively induce immune tolerance is the low pH of the stomach, which may further modify the polypeptide fraction, abrogating its ability to induce tolerance.

Another factor involved in the failure of orally dosed allergen fragments to induce desensitization to future exposure may be the actual nature of the fragment itself. In vitro synthesis of fragments requires specific enzymes and conditions that may or may not result in the preparation of a biologically optimal formulation. The fragment may be effective when it is acutely exposed to the immune system following intravenous administration, but may be so susceptible to modification that any alterations occurring in the gastrointestinal tract before its exposure to the appropriate immune system components may destroy its effectiveness.

A need exists, therefore, for an oral formulation of allergen fractions that, when administered orally, is sufficiently active to induce tolerance but is not allergenic. A need also exists for methods of producing such products.

SUMMARY OF THE INVENTION

This invention embodies the discovery of a method of manufacture, method of use, and product by process. The generic form of the product, by process of this invention, is milk that contains polypeptide fractions of allergens. The specific product by process of this invention is the milk polypeptide fraction that contains polypeptide fragments of specific allergens.

Specifically, the invention is directed to a milk produced by an immunized milk-producing animal, such milk containing non-immunoglobulin polypeptide fragments of the allergens used to immunize the animal.

The invention is further directed to a food product containing the milk of the invention or an active fraction of said milk.

The invention is further directed to an oral vaccine for administration to an allergic subject for relief of the allergic response in such subjects, such vaccine containing the milk of the invention or an active fraction thereof.

The invention is further directed to a method for the production of an immune suppressive product comprising the immunization of a milk-producing animal and the collection of milk from such animal after such animal reaches an immune state.

The invention is further directed to a method for the desensitization of a subject to an allergen which method comprises administration of the milk of the invention, or an active fraction there, to such subject, in an amount and for a time sufficient to produce an immune suppressive effect.

The invention is further directed to pharmaceutical compositions which provide to a subject who is in need of desensitization to an allergen, the active, polypeptide fragment-containing fractions of the invention at amounts which are efficacious in the treatment and suppression of such subject's allergic responses and allergic reactions.

DESCRIPTION OF THE PREFERRED EMBODIMENTS

The invention provides an oral formulation for desensitization, an oral vaccine, which is of significant medical benefit to the subject who ingests it. By subject is meant a human or other animal in need of allergy desensitizing according to the method of the invention. The oral vaccine of the invention can be self administered, is less painful, and less expensive then vaccines which must be injected. The subject ingesting the oral vaccine of the invention is exposed to the allergen in a derivatized, processed form which allows such subject to acquire tolerance to such allergen.

The milk of the invention, or an active fraction thereof, may be administered in any form which retains the allergic response suppressive properties of the milk, either powdered or liquid. Any food product which incorporates the active fractions of such milk may also be provided, for example, skim milk, yogurt and cheese.

By an "active fraction" of the milk of the invention is meant a preparation or composition which has been extracted from the milk of the invention and which retains the beneficial, allergic reaction-suppression properties of the unextracted milk of the invention which are due to the presence of derivatized, processed forms of the allergen used to immunize such animal providing such milk.

The derivatized, processed form of the allergen of the invention is found in the milk of a milk-producing animal which has been immunized against the allergen. The advantage of administering the polypeptide fraction of the invention to a subject rather than administering the unprocessed allergen itself is that, unlike the unprocessed allergen, the allergic response suppressive polypeptide fraction of the milk of the invention is nonallergenic. Desensitization of the subject who ingests the milk of the invention occurs but there is no risk of severe-allergic reactions in such subject because the allergen has been processed to a non-allergic form by the immune system in the milk-producing host.

The allergen which is used as a source of the immune suppressant active polypeptides can be any allergen which is capable of provoking an immune system response in the mammalian animal which processes such allergen. If an allergen is not capable of inducing an immune system response in one mammalian species, another species may be used. In a preferred embodiment, the milk-producer bovine dairy cow is used to process the allergen. However, any mammalian species may be used, including humans, and animals in the ovid, porcine, and equine species, etc.

The allergen preparation may contain a mixture of allergens or only one specific allergen. Examples of allergen mixtures which may be protected against by the administration of the milk preparation of the invention include mixtures of pollens of various trees and grasses, venoms from animals and insects, and food allergens. Examples of specific allergens which may be protected against by the administration of the preparation of the invention include, for example, ragweed, bee venom, and wheat protein in the case of a food allergy.

The method of manufacture of the polypeptide fraction of this invention produces a unique subfraction of the parent allergen, such subfraction exhibiting immune suppressive activity when used to treat a host allergic to such allergen. By "immune suppressive activity" is meant the ability of a composition to lessen allergic symptoms or allergic responses in an allergic subject who is administered such composition. By "allergic symptoms" is meant physiological reactions or conditions which are induced in an individual in response to that individual's being exposed to substances which are allergic for that individual, such as, for example, allergy-induced congestion, headaches, breathing, itching, swelling, sneezing, wheezing, coughing, rhinorrhea, and decreased ability to smell and taste.

The milk composition of the invention, and polypeptide fractions produced therefrom according to the process of this invention, lack the allergenicity of the parent allergen (the allergen used to immunize the milk-producing animal) but possess the ability to desensitize a host administered such compositions.

It is not necessary that the milk-producing animal be induced to, or maintained in, a hyperimmune state to produce the milk of the invention. Further, it is not necessary that the milk-producing animal be induced to an antibody-producing state to produce the milk of the invention because the active compositions of the invention do not rely on antibodies to provide their protective and suppressive activity. It is only necessary that the allergen-administered animal be provided with time sufficient to process such allergen into a form which is secreted in the milk of the animal.

Because immune cell processing of the allergen is one of the earliest steps in the immune response, milk containing the active polypeptides of the invention may be obtained relatively soon after administering the allergen, for example, 24 hours to a week after allergen administration. Cows administered allergen according to the method described herein provide such active polypeptides in their milk 24 hours after allergen administration.

Any amount of the allergen which results in the appearance of the active polypeptides of the invention in the milk of such animal may be administered to the milk-producing animal. If the amount of such active polypeptides in the milk of the allergen-administered animal is too low to provide efficacious benefits to a subject in need of desensitization, such active polypeptides may be provided to the subject in a more concentrated form. Such concentration is obtainable using techniques known in the art, for example, by salt precipitation, evaporation or lyophilization of the compositions of the invention.

Active polypeptide-containing preparations may be combined from more than one allergen-administered animal, and from more than one species of allergen-administered animal so as to provide the subject who is in need of desensitization with a composition containing a variety of polypeptide subfractions from different genetic heritages.

Although inducing a milk-producing animal to an antibody producing state or to a hyperimmune state is not necessary, neither is it detrimental to the milk of the invention and continuous production of milk containing the active polypeptides of the invention may be achieved by repeatedly administering the allergen to the milk-producing host.

Without meaning to be held to this theory, since the processing mechanism of the immune system is not fully understood, it is thought that the foreign protein or polypeptide is ingested or phagocytized by special cells of the immune system, the most noteworthy of which are the macrophage and neutrophil. After administration to a milk-producing animal, enzymes within the immune cell break down or derivatize the protein or polypeptide allergen into forms herein interchangeably termed "processed" forms or "subfractions" of the allergen.

The immune cell-produced subfractions are unique and cannot be produced outside of the natural host. The uniqueness is based first on the structure of the parent allergen and second on the combination of enzymes contained in the mammalian host's allergen processing cells. The enzyme combination which is expressed in the mammalian allergen processing cells are genetically determined; other species each have a unique combination of enzymes. For example peptide fractions of allergens processed by the immune cells of the bovine species are similar, but not identical, to polypeptide fractions processed by the immune cells of other species. It is because of this genetic specificity that the polypeptides produced by the process of this invention are unique and different from polypeptides produced by any other method.

Special immune cells called helper cells assist the macrophage in presenting the processed antigens to T and B lymphocytes. The passage of the allergen subfraction with and/or from the macrophage through the blood and across the mammary gland and into the milk may further modify the structure of the allergen polypeptide found in milk. This natural biological method of processing environmental antigens and transporting natural immune suppressants into the milk provides a mechanism whereby the dairy cow transfers immune protective factors to the calf through milk. These milk immune factors protect the nursing young of such animals against allergic reactions. Nature, through the process of evolution, has found a method for the mother of the species to sample the environment for potential allergens. The immune system then transforms the environmental allergens into the factors that protect against allergic reactions. The mother passes the immune protective factors to the nursing infant through milk. The essence of the discovery of the invention is that man can utilize this natural biological process to transform known allergens into immune protective polypeptide fractions that have utility for preventing and treating allergic reactions.

The milk immune suppressive factor is a polypeptide subfraction found in milk and not the antibodies found in milk. Although it is probable that antibodies are useful in treating allergies, milk antibody is not the product of this invention.

The milk of animals treated by the process of this invention contains specific and unique polypeptide subfractions of the allergens used to treat the host. The same milk lacks the intact or underivatized parent allergen. The uniqueness of these polypeptide fractions results from specific enzymatic breakdown by specialized immune cells of the host. Blood and mammary tissue enzymes may also play a role in modifying the chemistry of the allergens before entry into the milk. Milk containing these unique nonreactive polypeptides is useful as an oral immune treatment for inducing protection and/or tolerance when fed to other species including man. The milk allergen polypeptide fractions, when isolated from the milk, are useful for suppressing allergic reactions against the representative parent allergens.

The allergen may be administered to the milk-producing animal by various routes of administration including oral, rectal, vaginal, intramuscular injection, subcutaneous injection, intradermal injection, transcutaneous administration, etc. While, any route of treatment can be used for administering the allergen, the preferred route of treatment is by intramuscular injection of the allergen into the host species. The allergen, upon entry into the body of the milk-producing animal, is processed by the immune system of the milk-producing host.

Treatment of the allergic individual or animal with the compositions of the invention effects protection in that individual or animal against the parent allergen without danger of side effects that may occur when the parent molecule is used. Examples of protein or polypeptide allergens that can be processed by the mammalian milk system of mammals include pollen allergens of weeds, grasses and trees, animal venoms and poisons, and various food allergens. In a preferred embodiment, the bovine milk system is used. Theoretically, any allergen can be processed by the mammalian, and especially by the bovine, macrophage system to produce immune suppressive polypeptide subfractions.

The process of this invention is advantageous because it uses the full spectrum of processing enzymes available in the allergen processing cell of the mammalian immune system. A second advantage of the process of this invention is that the full spectrum of polypeptide fractions is contained in the immune suppressive milk product and the immune suppressant allergen fractions, when contained in a natural milk vehicle, are orally active. The process of this invention, does not require selection of specific enzymes to degrade the allergen in vitro or regulation of the enzymatic digestive process, nor does the process of this invention require separation of the enzymes and residual parent molecules from the reaction system. The entire antigen processing occurs naturally within the body of the milk-producing animal. The genetics of the mammal selects the enzymes and the natural metabolism of the mammal maintains reaction conditions at an optimal level for antigen processing.

The peptide fractions of the invention may be monitored, purified and isolated by any technique or combination of techniques wherein such peptides retain their bioactivity, that is, wherein such peptides retain the ability to suppress allergic responses. Such techniques are known in the art and include, but are not limited to, chromatographic techniques, including adsorption chromatography, gel chromatography and especially, gel chromatography through a dextran, polyacrylamide, or agarose matrix, ion-exchange chromatography, for example, utilizing a strong cationic exchanger such as, for example, SP-Sephadex (which contains a sulfopropyl functional group derivatized to a dextran), AG 50 (which contains a sulfonic acid derivatized to styrene-divinyl-benzene), and Bio-Rex 40 (which contains a sulfonic acid functional group derivatized to a phenolic matrix); weak cationic exchangers, such as, for example, CM-Sepharose (which contains a carboxymethyl functional group derivatized to a dextran), Bio-Rex 70 (which contains a carboxylic functional group derivatized to a phenolic matrix); strong anionic exchangers, such as, for example, QAE-Sephadex (which contains a diethyl-(2-hydroxypropyl)-aminoethyl functional group derivatized to a dextran), AG 1 (which contains a tetramethylammonium ion functional group derivatized to styrene-divinylbenzene); weak anionic exchangers, such as, for example, DEAE-Sephadex (which contains a diethylaminoethyl functional group derivatized to a dextran, AG-3 (which contains a tertiary amino functional group derivatized to an epoxyamine matrix); medium strength cationic exchangers, such as, for example, CM-cellulose (which contains a carboxymethyl functional group derivatized to cellulose), P-cel (which contains a phospho- functional group derivatized to cellulose); and medium strength anionic exchangers, such as, for example, DEAE-cellulose (which contains a diethylaminoethyl functional group derivatized to cellulose), PEI-cellulose (which contains a polyethyleneimine functional group derivatized to cellulose, DEAE(BND)-cellulose (which contains a benzoylated-naphthoylated, diethylaminoethyl functional group derivatized to cellulose), PAB cellulose (which contains a p-aminobenzyl functional group derivatized to cellulose); and, exchangers which provide a mixture of functional groups, such as, for example, AG501 (which contains two functional groups, sulfonic acid and tetramethylammonium ion derivatized to a styrene-divinyl benzene matrix). In addition, high pressure liquid chromatography, may be used to separate the peptides of the invention.

Other compounds may be conjugated, either chemically or by genetic engineering, to the active polypeptides of the invention so as to enhance or provide additional properties to such polypeptide-containing compositions, especially properties which enhance the active polypeptide's ability to promote relief of an allergen's effects in a subject in need of immune suppressive treatment.

Amounts and regimens for the administration of the compositions of the invention can be determined readily by those with ordinary skill. Generally, the dosage of the active peptide-containing composition will vary depending upon considerations such as: type of allergen employed; age of the subject being treated; health of the subject being treated; type of allergy being treated; kind of concurrent treatment, if any; physiological tolerance to the compositions of the invention; frequency of treatment and the nature of the effect desired; gender; duration of the symptoms; and, counterindications, if any, and other variables as may be adjusted, as desired, by the individual's physician. Dosage can be administered in one or more applications to obtain the desired results.

The compositions of the invention can be administered in any appropriate pharmacological carrier for administration. They can be administered in any form that effects prophylactic, palliative, preventative or curing conditions of allergic reactions in humans and animals.

Preparations of the active polypeptide-containing compositions of the invention for parenteral administration includes sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The compositions of the invention may also be administered by means of pumps, or in sustained-release form.

Administration in a sustained-release form is more convenient for the patient when continuous repeated administration for prolonged periods of time are indicated.

The active polypeptide-containing compositions of the invention can be employed in dosage forms such as tablets, capsules, powder packets, or liquid solutions for oral administration.

The pharmaceutical compositions of the present invention are manufactured in a manner which is in itself know, for example, by means of conventional mixing, granulating, dragee-making, dissolving, lyophilizing or similar processes.

Having now generally described the invention, the following examples further describe the materials and methods used in carrying out the invention. The examples are not intended to limit the invention in any manner.

EXAMPLES

Example 1
Immunization of Cows and Collection of Immune Milk

The immunogen for the preparation of the milk product for allergy symptom alleviation comprises a mixture of commercial allergen extracts purchased as 1:100 wt:vol preparations and pooled in the following ratios:

| ALLERGEN | Volume (ml) |
|---|---|
| *Alternaria tenuis* | 10 |
| *Aspergillus niger* | 10 |
| *Monilia albicans* | 10 |
| *Hormodendrum hordei* | 10 |
| Lambs quarter | 10 |
| House dust | 10 |
| Helminthosporium Sat. | 10 |
| Russian thistle | 10 |
| Careless weed | 10 |
| Spiny pigweed | 10 |
| Mugwort, common | 10 |
| Ragweed, slender | 10 |
| Ragweed, southern | 10 |
| Ragweed, false | 10 |
| Ragweed, short | 10 |
| Ragweed, giant | 10 |
| Pigweed, redroot | 10 |
| *Trichophyton mentag* | 10 |
| Goldenrod | 10 |
| Palmer's ameranth | 10 |
| Sage, prairie | 10 |
| *Curvularia spisifera* | 30 |
| *Pullularia pullulans* | 30 |
| *Mucor plumbeus* | 30 |
| *Fusarium moniliforme* | 30 |
| GS Mold Mix #2 | 30 |
| GS 10 Tree Mix | 30 |
| *Rhizopus nigricans* | 30 |

The pooled mixture is diluted with an equal volume of sterile saline. Cows are injected intramuscularly with 5 ml of the preparation at 2 week intervals during normal lactation, and the milk is collected and powdered. Milk is collected beginning 24 hr. post treatment.

Example 2
Fractionation of Milk Fractions Containing Processed Allergens

Twenty liters of fresh milk from hyperimmunized cows were run through a cream separator (DeLaval Model 102) to remove the fat.

The resulting sixteen liters of skimmed milk was ultrafiltered to remove the high molecular weight species (over 100,000 daltons) using a hollow fiber diafiltration/concentrator. The concentrator is equipped with two 100,000 daltons molecular weight cut-off cartridges. The skimmed milk was run at the pump speed of 80 on the meter and inlet and outlet pressure of 30 psi and 25 respectively.

Twelve liters of the filtrate (<100,000 daltons) coming out of the cartridges at the flow rate of four liters per hour was frozen or lyophilized for storage.

The same methods may be used to fractionate the milk from non-hyperimmunized cows.

Example 3

Desensitization of Allergic Subjects

Human volunteers consumed approximately ½ cup of the immune milk powder reconstituted with 8 oz of water. Two hundred volunteers ranged in age from 4 to 87 years, and drank the milk for 1 to 172 months. Of 168 subjects with allergies who submitted responses indicating the status of their condition, 138 (82.1%) indicated that they had improved while drinking the milk. Ninety-four percent of subjects reporting benefits stated their improvement occurred within 1 month of starting to drink the milk. Specific effects reported included less congestion, fewer or no headaches, easier breathing, less itching, swelling, sneezing, wheezing, coughing, rhinorrhea, and an enhanced ability to smell and taste. Many subjects reported a recurrence of symptoms of milk consumption was stopped, and several subjects discontinued allergy immunotherapy after drinking the milk.

Having now fully described the invention, it will be understood by those with skill in the art that the scope may be performed within a wide and equivalent range of conditions, parameters and the like, without affecting the spirit or scope of the invention or any embodiment thereof.

What is claimed is:

1. An oral vaccine, wherein said vaccine comprises a composition wherein said composition comprises a non-antibody fraction of milk and wherein said non-antibody fraction of milk ameliorates, in a subject with an allergy to an allergen, the symptoms of said allergy of said subject to said allergen when said fraction is ingested by said subject and wherein said fraction is produced by the process comprising:

(a) administering said allergen to a milk-producing animal;
    (b) collecting the milk from said animal of part (a);
    (c) filtering the milk of part (b) through a filter which excludes molecules of greater than 100,000 daltons; and
    (d) collecting the effluent from the filtration of part (c) wherein said effluent contains said fraction.

* * * * *

UNITED STATES PATENT AND TRADEMARK OFFICE
CERTIFICATE OF CORRECTION

PATENT NO.   : 5,814,345
DATED        : September 29, 1998
INVENTOR(S)  : Beck et al.

It is certified that error appears in the above-identified patent and that said Letters Patent is hereby corrected as shown below:

Title page,
Item [22], delete "Jun. 21, 1995" and insert therefor -- Jun. 2, 1995 --.

Column 2,
Line 32, delete "does" and insert therefor -- dose --.

Column 4,
Line 11, delete "are" and insert therefor -- is --.

Column 5,
Line 9, delete "there" and insert therefor -- thereof --.
Line 26, delete "then" and insert therefor -- than --.

Column 10,
Line 6, delete "know" and insert therefor -- known --.

Column 11,
Line 22, delete "of" second occurrence and insert therefor -- after --.

Signed and Sealed this

Fourth Day of December, 2001

Attest:

*Attesting Officer*

NICHOLAS P. GODICI
*Acting Director of the United States Patent and Trademark Office*